United States Patent [19]

Zimmerman et al.

[11] Patent Number: 6,121,422
[45] Date of Patent: Sep. 19, 2000

[54] METHOD AND DEVICE FOR DELIVERING FIBRIN GLUE

[75] Inventors: Thomas P. Zimmerman, Raleigh; Christopher A. Dadd, Cary; George A. Baumbach, Knightdale, all of N.C.

[73] Assignee: Bayer Corporation, Berkeley, Calif.

[21] Appl. No.: 09/200,636

[22] Filed: Nov. 25, 1998

Related U.S. Application Data

[62] Division of application No. 08/744,488, Nov. 5, 1996, Pat. No. 5,844,087.

[51] Int. Cl.$^7$ .............................. A61K 35/14; A61M 5/00; B01D 63/00
[52] U.S. Cl. ...................... 530/381; 530/382; 530/384; 530/402; 604/187; 604/188; 604/196
[58] Field of Search ..................................... 530/381, 382, 530/384, 402; 604/187, 188, 196

[56] References Cited

U.S. PATENT DOCUMENTS

| | | | |
|---|---|---|---|
| 4,377,572 | 3/1983 | Schwarz et al. | 424/101 |
| 5,393,666 | 2/1995 | Linnau | 435/183 |
| 5,674,394 | 10/1997 | Whitmore | 210/321.8 |
| 5,739,288 | 4/1998 | Edwardson et al. | 530/382 |

*Primary Examiner*—Christopher S. F. Low
*Assistant Examiner*—Abdel A. Mohamed
*Attorney, Agent, or Firm*—Michael J. Beck; James A. Giblin

[57] ABSTRACT

A method and device for activating and applying a solution of fibrinogen to form fibrin glue at a desired site. The method includes contacting the solution of fibrinogen with immobilized thrombin under conditions that result in a solution of polymerizable fibrin and delivering the activated solution to the desired site. The device includes a housing having a compartment for a solution of fibrinogen, a container for immobilized thrombin, a structure following the solution of fibrinogen to be brought into contact with the immobilized thrombin under conditions which permit the activation of the fibrinogen to polymerizable fibrin, and a structure allowing for delivery of the activated solution to the desired site.

7 Claims, 3 Drawing Sheets

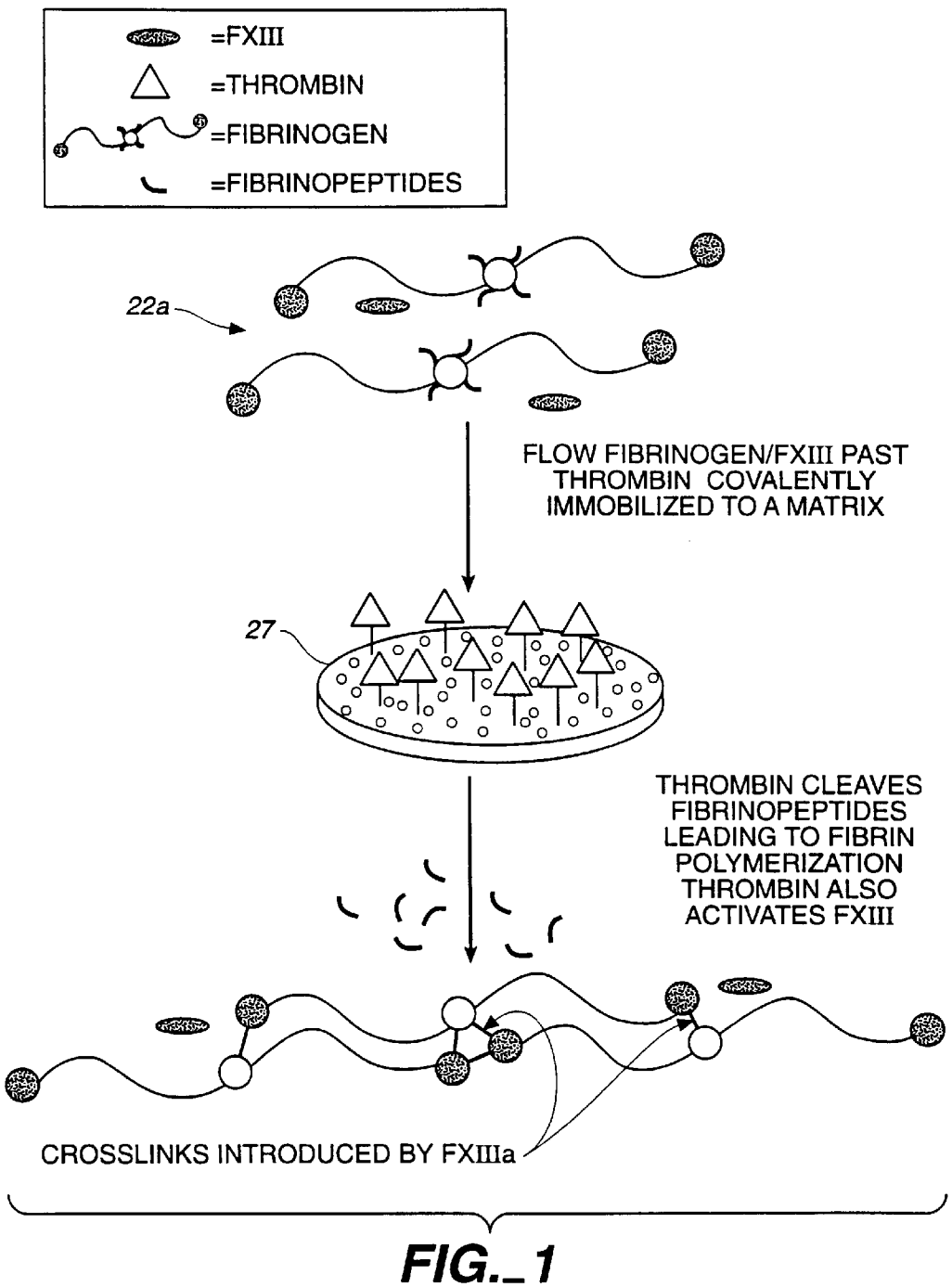
FIG._1

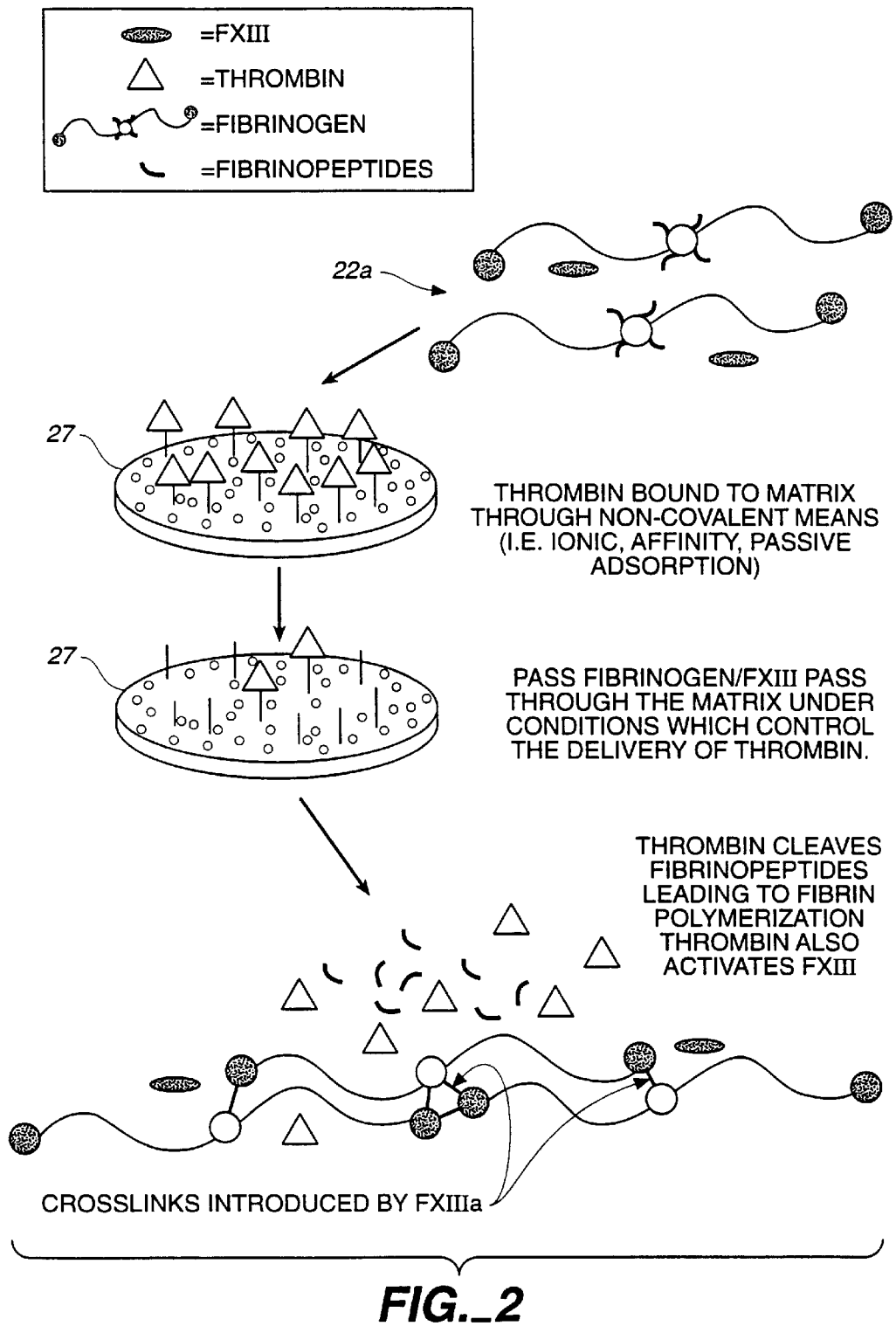
FIG._2

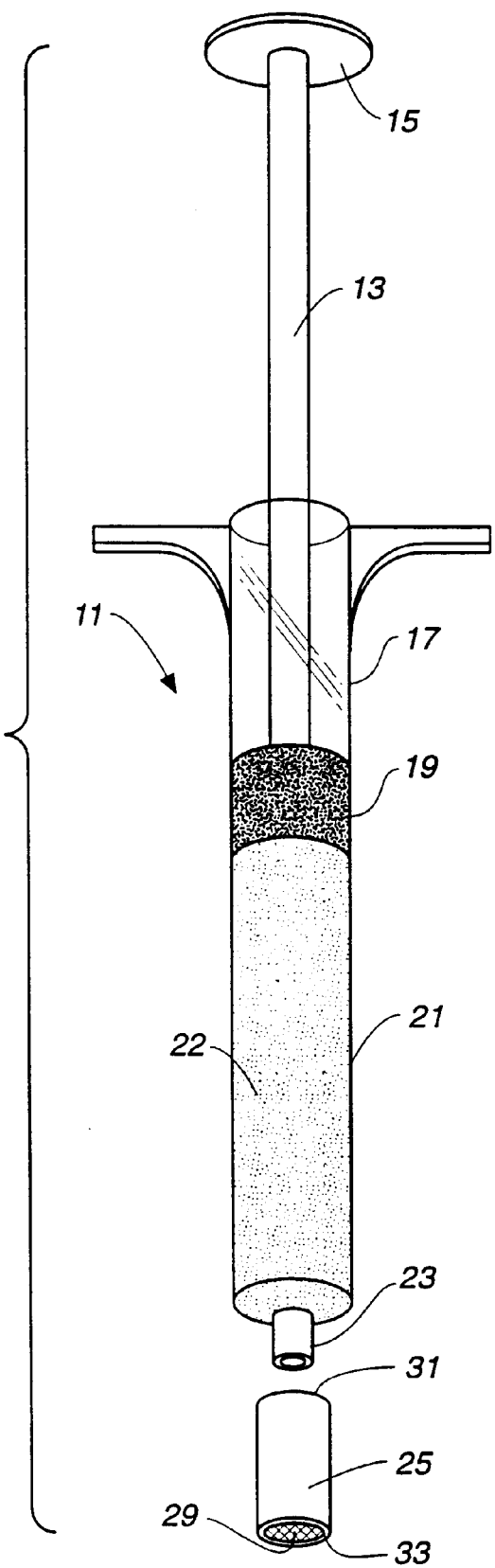
FIG._3

METHOD AND DEVICE FOR DELIVERING FIBRIN GLUE

This is a divisional application of U.S. Ser. No. 08/744,488, filed Nov. 5, 1996, now U.S. Pat. No. 5,844,087. The parent application, U.S. Ser. No. 08/744,488 is herein incorporated by reference.

BACKGROUND OF THE INVENTION

1. Field

The present invention relates generally to fibrin glue, also known as tissue adhesive or fibrin sealant. More specifically, the invention relates to a delivery system which permits contact of a fibrinogen-containing solution with thrombin to form polymerizable fibrin prior to delivery of the solution to a site.

2. Background

Fibrin glues have been known for many years. For example, U.S. Pat. No. 2,533,004 to Ferry shows the use of varying concentrations of fibrinogen solution in conjunction with a thrombin solution for forming fibrin clots.

In addition to its principal ingredients, α-thrombin and fibrinogen, fibrin glue may contain a small amount of factor XIII, which co-purifies with the fibrinogen when purified from human plasma. In the presence of thrombin, soluble fibrinogen is converted into soluble fibrin which self-polymerizes into an insoluble matrix. Thrombin also converts factor XIII into factor XIIIa. The latter cross-links the fibrin matrix to give a highly crosslinked polymer, which contributes to the effectiveness of the tissue adhesive or fibrin glue. The adhesive preparations allow for reliable stopping of bleeding, make for good adhering capacity to the wound or tissue surfaces, provide for high straining capacity of the glued sites or sealed wounds, and provide for complete absorbability of the tissue adhesive in the course of wound healing. Fibrin glues have been used for control of bleeding (hemostasis), for augmentation or replacement of sutures or wound clips, for adhering skin grafts, for sealing puncture wounds, for sealing and adhering catheters, and even for use as a depot for drug delivery.

The fibrinogen and α-thrombin must be formulated in a manner that stabilizes and completely separates these two proteins until the time of their actual use. Because α-thrombin is an activated protease, it is particularly difficult to store stably in solution. U.S. Pat. Nos. 4,298,598 and 4,377,572 to Schwartz et al. and 4,909,251 to Seelich, e.g., show examples of compositions of fibrin glue preparations.

Existing commercial formulations for fibrin glue include separated frozen or lyophilized preparations of α-thrombin and fibrinogen prepackages in a dual syringe. The frozen formulations require that the product's two ingredients be stored and shipped in the frozen state. Finally, the dual syringe used to dispense existing fibrin glues is somewhat bulkier and more difficult to handle than a conventional syringe and may feel awkward to use.

Various types of applicators are disclosed in the prior art. For example, U.S. Pat. No. 4,359,049 to Redl discloses a syringe-type apparatus which includes a plurality of syringe bodies and a connecting head with a single needle.

An improved design applicator was disclosed in U.S. Pat. No. 4,974,368 to Miller. This applicator includes a pair of syringe tubes which can be actuated together or separately, a member which holds the syringes parallel to each other, and a double needle assembly which allows separate delivery of the components of the fibrin glue to the treatment site.

Another device uses syringes with barrels having different cross-sectional area, thus altering the relative quantities of the components. See U.S. Pat. No. 4,735,616 to Eibl which shows one syringe cross section having an area 2 to nine times larger then the second syringe.

Single-syringe fibrin sealants have been described. For example, in one application a mixture of fibrinogen and prothrombin is contained in a single syringe and clot formation occurs by action of endogenous factor Xa at the wound site. See also patents for light-reversible, inhibited thrombin together with fibrinogen (U.S. Pat. Nos. 5,219,328 and 5,318,524, both to McNally et al.; PCT/U.S. 91/00003).

At the 1995 Thrombosis and Hemostasis Meeting, there were two reports (Abstract Nos. 2150 and 2174) of novel fibrin monomer formulations which could be envisioned as a single-syringe glue. Batroxobin was used instead of thrombin to form soluble fibrin monomers and batroxobin was then removed by affinity chromatography. However, batroxobin, in contrast to thrombin, cleaves only fibrinopeptide A from fibrinogen and does not cleave fibrinopeptide B from fibrinogen or activate factor XIII.

U.S. Pat. No. 5,393,666 to Linnau discloses a method of activating prothrombin by means of trypsin, wherein the prothrombin is treated with trypsin immobilized on a water insoluble carrier and then is separated from the immobilized trypsin after activation.

A principal challenge in designing a single-syringe delivery system for fibrin glue is the need to separate completely the solution of fibrinogen from an activating protease, most preferably α-thrombin, until the moment of the use of the fibrin glue. With solutions of fibrinogen and thrombin, fibrin glue can only be generated in a controlled manner by using a dual-syringe system that effectively separates the fibrinogen from its activating protease until the desired time of glue generation.

To the best of our knowledge, no one has previously proposed the use of an immobilized protease cartridge, for attachment to a syringe tip, to activate fibrinogen and to thereby allow the delivery of the activated solution of polymerizable fibrin with a single syringe.

SUMMARY OF THE INVENTION

Our invention includes a method comprising the steps of contacting a solution of fibrinogen (preferably with factor XIII) with a preparation of immobilized thrombin under conditions resulting in an activated solution of soluble polymerizable fibrin, and applying the soluble fibrin to a desired site such as a wound site. The immobilized thrombin cleaves the fibrinogen to fibrin and proteolytically activates factor XIII (if present) thus allowing the fibrin glue to be delivered in liquid form to the site of application, where polymerization of the fibrin monomers and subsequent cross-linking will produce the desired tissue adhesive in a timely manner.

Our invention further comprises an apparatus for bringing the components of the fibrin glue together for activation and delivery. Our invention is particularly suited to providing a method for delivering fibrin glue from an apparatus or device such as a single syringe. A one-syringe delivery system can be used more conveniently than the bulkier dual-syringe systems to apply fibrin glue to wound sites.

BRIEF DESCRIPTION OF THE FIGURES

FIG. 1 illustrates the passage of fibrinogen over thrombin covalently bound to a matrix.

FIG. 2 illustrates a process similar to FIG. 1 except that the thrombin is noncovalently immobilized to the matrix thereby permitting at least some of the thrombin to be released for flow through the matrix with the fibrinogen molecules.

FIG. 3 illustrates a syringe-like device found useful in employing the methods of this disclosure.

SPECIFIC EMBODIMENTS

Materials and Methods

Materials

Human thrombin and fibrinogen were purchased from Enzyme Research Labs (South Bend, Ind.). SP SEPHAROSE Fast Flow® cation exchange resin was purchased from Pharmacia (Piscataway, N.J.). POLYPREP columns and nitrocellulose were from Bio-Rad (Hercules, Calif.). Surfactant-free cellulose acetate (SFCA) syringe-tip filters, 25 mm, 0.2 μm, were from Nalge Nunc International (Rochester, N.Y.). Tuberculin syringes were purchased from Becton Dickenson (Franklin Lakes, N.J.). ACTI-DISK® 50 Glutaraldehyde (GTA) membrane cartridges were purchased from Whatman (Hillsboro, Oreg.). All other chemicals were reagent grade or better.

General Methods

Covalent Immobilization of Thrombin to a Glutaraldehyde-Activated Membrane

A 50 mm GTA membrane cartridge was prepared for covalent attachment of α-thrombin. The membrane was washed with water and equilibrated with 10 mM sodium citrate pH 7.2. A peristaltic pump was used to recirculate 53,418 Units (1709 Units/ml; 560 μg/ml) of α-thrombin in 25 mM sodium citrate, 100 mM NaCl, 0.05% PEG, pH 6.5 through the GTA cartridge at 1.8 ml/min for 1.5 hr. at room temperature. As determined by $A_{280}$ before and after crosslinking and washing, 64% of the applied α-thrombin was covalently crosslinked to the membrane. This represents 11.2 mg of thrombin with an activity of 34,187 Units (assuming 100% activity). Free membrane binding sites were blocked with 1 M Tris pH 7.8 followed by 1 M ethanolamine pH 7.8. Both were recirculated for 1 hr at 1.8 ml/min at room temperature.

Adsorption of Thrombin on SP SEPHAROSE Fast Flow® Cation Exchange Resin

α-Thrombin (3055 Units) was adsorbed to 5 ml of cation exchange chromatography resin, SP-SEPHAROSE Fast Flow®, in a column format. The resin was equilibrated with 10 ml of 50 mM sodium phosphate pH 7.8 prior to thrombin adsorption. The α-thrombin was added to the resin in a 10 ml POLYPREP column and allowed to bind for 10 min at room temperature. The resin was washed with 10 column volumes of 50 mM sodium phosphate pH 7.8.

Adsorption of Thrombin on Nitrocellulose

A 25 mm circular disk of nitrocellulose (BioRad) was placed in a solution of 411 μg α-thrombin (Enzyme Research Labs), equivalent to 1256 Units, and shaken at room temperature for 20 min. The nitrocellulose was washed 3 times, 2 min each, in 200 ml PBS (100 mM sodium phosphate, 150 mM NaCl pH 7.4) at room temperature to remove unbound thrombin.

DETAILED DESCRIPTION OF THE FIGURES

The principles of this disclosure can be understood by reference to the Figures. FIG. 1 illustrates in a very general way how fibrinogen molecules 22a in an aqueous solution which preferably also includes FXIII molecules flow through or contact an immobilization matrix 27 which includes covalently bonded thrombin molecules in a biologically active form (able to cleave the fibrinopeptides from the fibrinogen molecules 22a). After passage through or contact with the thrombin bonded to immobilization matrix 27 the fibrinopeptides are cleaved from the fibrinogen 22a, resulting in polymerizable fibrin molecules. Activated FXIII (FXIIIa) then introduces cross-links into the polymerizing fibrin.

FIG. 2 illustrates the same general flow as FIG. 1 except that the thrombin is adsorbed to the water insoluble support materials that form the matrix. This looser bonding permits at least some of the thrombin molecules to be carried with the fibrin molecules for subsequent activation of FXIII (if present).

FIG. 3 illustrates a syringe-like device that was used to demonstrate the principles of this disclosure. FIG. 3 comprises a single barrel syringe 11 consisting of a syringe body 17 and syringe plunger 13 having a thumb-push plate 15 and a plunger head 19 positioned above liquid chamber 21 which includes a solution of fibrinogen 22. Syringe 11 terminates at its lower end in an exit port 23 which is connectable (e.g. by a securable friction or Iver fitting) to a cartridge 25 having an input port 31 (not shown), an exit port 33, and a retaining screen 29. Within cartridge 25 is the matrix and immobilized thrombin such as that illustrated in FIGS. 1 and 2. It can be appreciated that the immobilized thrombin retained within cartridge 25 can be on a variety of well known supports such as resin beads, porous glass particles, disks adapted for immobilization of proteins, nitrocellulose particles or disks, etc. The main requirements are that the fibrinogen solution 22 be capable of flowing through the cartridge 25 as plunger head 19 pushes fibrinogen solution 21 out of syringe 11 when pressure is applied to thumb plate 15 and the flow through should be under conditions that permit ready contact of the fibrinogen with the immobilized thrombin.

In a working example demonstrating the principles of the invention, we used a commercially available ACTI-DISK® cartridge and immobilized the thrombin in the existing cartridge system. In another two examples, we introduced the immobilized thrombin matrix into a commercial filter cartridge. The main requirement for the cartridge 25 is that is be affixable to the delivery tip of a syringe and be capable of retaining the immobilized support material for the immobilized thrombin when the fibrinogen solution 22 is passed though it. Again, the thrombin may be immobilized by covalent or noncovalent bonds as illustrated in FIGS. 1 and 2 and the examples below.

Alpha-thrombin is formulated as a stable, immobilized preparation bound to a suitable solid matrix. In one embodiment of the invention, the immobilized thrombin is contained in a compact, replaceable cartridge that can be securably affixed to the Iver tip of a standard syringe. Fibrinogen is formulated and supplied as a stable solution, preferably in a syringe with a Iver tip and may be frozen to assure stability. At the time of use, the fibrinogen solution is warmed to ambient temperature in it syringe, a cartridge of immobilized α-thrombin is affixed to the exit tip of the syringe, and the fibrinogen solution is extruded from the syringe barrel through the α-thrombin-containing cartridge for delivery of fibrin glue to a wound site. Should discontinuous use of an α-thrombin-containing cartridge result in clogging of the exit port with fibrin clot, the blocked cartridge can simply be replaced by a fresh cartridge to allow continued application of fibrin glue using the residual fibrinogen solution contained in the syringe barrel. This design minimizes preparation time of the fibrin glue syringe, allows the delivery of fibrin glue from a single syringe, and provides the user (e.g. surgeon) with an compact syringe applicator of familiar size and feel. As an additional advantage, this unique product design will not require concommitant formulation with protease inhibitors such as aprotinin.

The α-thrombin protease used to activate fibrinogen and factor XIII can be immobilized either covalently or noncovalently to a suitable solid support or it can be in the form of with CLEC cross-linked enzyme crystals that are contained within a permeable chamber. It is thought that the protease could be immobilized covalently to solid supports of a variety of configurations (e.g., beads, membranes, filters, etc.) and compositions (e.g., glass, nitrocellulose or other cellulosic material, polystyrene, polypropylene, polyhydroxylated methacrylate, cross-linked agarose, dextran, etc.) while retaining substantial biological activity. When the protease is immobilized covalently, it will be retained completely on its solid, water-insoluble support and will not be extruded to the wound site when the fibrin glue is applied.

The activating protease can also be immobilized noncovalently to a solid support on the basis of chemical or physical attractive forces between the protease and its support. These attractive forces can be of the nature of complementary molecular structures (e.g., antibody-antigen interactions, metal ion-binding, carbohydrate binding to a boronate resin or to an immobilized lectin, or other forms of affinity chromatography) or adsorption based on surface physical properties (e.g., hydrophobicity, charge, hydrogen bonding, etc.).

In the case of noncovalent attachment of the protease to its support, conditions can be devised whereby the protease either is retained bound to it support or is partially or totally released during passage of the fibrinogen solution over the support-bound protease. For some applications it may be preferable to allow the coextrusion of the protease and fibrin/fibrinogen from the cartridge tip to the wound site in order to optimize the quality of the resultant sealant.

Indeed, the ideal embodiment of this invention may include a combination of covalently and noncovalently immobilized activating protease. Regardless of whether the activating protease is bound covalently or noncovalently to its solid support, the rate of activation of fibrinogen to fibrin can be regulated by varying the amount of biologically active enzymatic catalytic sites present on the support.

EXAMPLE 1

Cleavage of Soluble Fibrinogen to Fibrin by Covalently Immobilized Thrombin

An ACTI-DISK cartridge containing immobilized (conjugated) thrombin was prepared as described above. The membrane was then washed with water for 10 min, 2.5 ml/min, room temperature and equilibrated with 20 mM sodium phosphate pH 7.8. As a negative control, 200 µl of this equilibrated solution was mixed with 300 µl fibrinogen at 10 mg/ml. No clotting was observed.

A 10 mg/ml solution of fibrinogen in 20 mM sodium phosphate, 150 mM NaCl, pH 7.8 was flowed through the ACTI-DISK® cartridge at 700 µl/min. The outlet material was collected. Approximately 3 ml of solution were passed through the cartridge (collected as 2 ml and 1 ml fractions). Both fractions clotted within 2 min. These experiments indicate that fibrinogen is being cleaved to fibrin as it passes through the membrane to which thrombin is covalently attached, resulting in fibrin polymerization external to the membrane cartridge.

EXAMPLE 2

Cleavage of Soluble Fibrinogen To Fibrin by Thrombin Adsorbed to SP-SEPHAROSE Fast Flow Cation Exchange Resin Thrombin was immobilized upon SP-SEPHAROSE Fast-Flow resin as described (see Materials and Methods). The thrombin-adsorbed resin (100 µl) was pipetted into a 0.2 µm SFCA syringe-tip filter followed by 100 µl of 50 mM sodium phosphate pH 7.8. A 1 ml sample of fibrinogen at 10 mg/ml in 100 mM sodium phosphate, pH 7.8 was loaded into a 1 cc tuberculin syringe. The ionic strength of the fibrinogen solution was such that when the solution contacted the cation resin, the thrombin was eluted.

When the fibrinogen was flowed past the thrombin-adsorbed resin, the material exiting the syringe and filter cartridge contained a mixture of fibrinogen/fibrin and thrombin resulting in the formation of a fibrin clot in approximately 30 seconds. A negative control resin without adsorbed thrombin showed no ability to clot the fibrinogen solution under the same experimental conditions. Passing a more dilute (1 mg/ml) solution of fibrinogen past a second aliquot of thrombin-adsorbed cation resin resulted in a clotting time of 45 seconds and a clot that appeared to be weaker. A decrease in the amount of thrombin-adsorbed cation resin (10 µl) loaded into the syringe-tip filter cartridge resulted in a clotting time of 1 min when a 10 mg/ml solution of fibrinogen was flowed part at the same ionic strength as above.

These experiments illustrate that thrombin, when adsorbed noncovalently to a certain exchange resin, can cleave fibrinogen, resulting in fibrin glue or clot formation. Moreover, the strength and time of clot formation can be varied by changing the amounts of fibrinogen and/or thrombin. Varied clotting properties may be useful for different applications.

EXAMPLE 3

Cleavage of Soluble Fibrinogen to Fibrin by Thrombin Immobilized on Nitrocellulose A nitrocellulose membrane having thrombin immobilized on it surface was prepared as described above. The nitrocellulose was mounted inside a 25 mm disposable filter cartridge, which had been cut open, and sealed with PARAFILM laboratory film. To test if thrombin was being washed off the membrane, 1 ml water was passed through the cartridge and collected into 500 µl of fibrinogen at 20 mg/ml. The material exiting the cartridge clotted the fibrinogen within 5 seconds. The above was repeated with four more 1 ml aliquots of water, resulting in respective clotting times of 20 sec, 45 sec, 2 min and 5 min.

A 1 ml solution of fibrinogen at 10 mg/ml (5 mM sodium citrate, 2.5 mM $CaCl_2$, pH 7.8) was then passed through the cartridge and collected as 14 separate fractions (one drop/fraction). The first three fractions did not clot; they likely contained little fibrinogen due to the hold-up volume of water in the cartridge. Fraction #4 contained a partial or weak clot probably due to a decreased fibrinogen concentration as a result of dilution by the hold-up volume water. Fractions 5 through 14 appeared to have equally strong clot formation after 1.5 min.

The above experiment was repeated without washing the nitrocellulose in PBS but rather passing 5 ml water through the cartridge containing the nitrocellulose. Again, 1 ml of a 10 mg/ml solution of fibrinogen was passed through the cartridge resulting in clot formation in 18 sec. These experiments indicate that thrombin adsorbed to nitrocellulose can cleave fibrinogen to fibrin resulting in clot formation.

Discussion

Fibrinogen must be cleaved proteolytically to fibrin monomer, the spontaneous polymerization of which leads to fibrin (glue). The stability and strength of the resulting fibrin glue are enhanced by cross-linking of the fibrin chains catalyzed by activated factor XIII (known as factor XIIIa). These examples show various means whereby both fibrinogen and factor XIII can be cleaved, and consequently activated, by α-thrombin when they are transiently exposed to the immobilized protease while being extruded from a syringe. Equivalent means may be used to accomplish essentially similar results.

It is thought that the invention disclosed here would have applications in other systems where an immobilized enzyme system could be used to catalyze other useful therapeutic reactions. For example, the administration of plasmin for thrombolysis, or the administration of activated coagulation factors (e.g., factors IIa, VIIa, VIIIa, Ixa, Xa, XIa, XIIa, XIIIa) for hemostatis, or the administration of activated protein C for anticoagulation could benefit from the application of this invention.

The above examples are intended to illustrate the invention and it is thought variations will occur to those skilled in the art. Accordingly, it is intended that the scope of the invention should be limited only by the claims below.

What is claimed is:

1. A method of applying an activated solution of polymerizable fibrin to a desired site, the method comprising:

a) affixing a cartridge containing immobilized thrombin to a syringe containing a solution of fibrinogen, b) contacting the solution of fibrinogen with immobilized thrombin under conditions resulting in an activated solution of polymerizable fibrin by passing the solution of fibrinogen through the cartridge containing immobilized thrombin, and c) delivering the activated solution of polymerizable fibrin to the desired site for a time and under conditions which result in polymerized fibrin at the site.

2. The method of claim 1, wherein the solution of fibrinogen further comprises factor XIII.

3. The method of claim 1, wherein the thrombin is immobilized by being attached to a solid support via a combination of covalant bonding and noncovalent bonding.

4. The method of claim 1, wherein the thrombin is immobilized by being covalently bonded to a solid support.

5. The method of claim 4, wherein the solid support comprises a material selected from the group consisting of glass, a cellulosic material, polystyrene, polypropylene, polyhydroxylated methacrylate, cross-linked agarose, and dextran.

6. The method of claim 1, wherein the thrombin is immobilized by being noncovalently bonded to a solid support.

7. The method of claim 6, wherein the solid support comprises a material selected from the group consisting of glass, a cellulosic material, polystyrene, polypropylene, polyhydroxylated methacrylate, cross-linked agarose, and dextran.

* * * * *